United States Patent
Sabliov et al.

(10) Patent No.: US 10,952,974 B2
(45) Date of Patent: Mar. 23, 2021

(54) DELIVERY OF BIOACTIVE, NANOENCAPSULATED ANTIOXIDANTS

(71) Applicants: Board of Supervisors of Louisiana State University and Agricultural and Mechanical College, Baton Rouge, LA (US); Iuliu Haţieganu University of Medicine and Pharmacy, Cluj-Napoca (RO)

(72) Inventors: Cristina M. Sabliov, Baton Rouge, LA (US); Carlos E. Astete, Baton Rouge, LA (US); Ede Bodoki, Cluj-Napoca (RO); Oliviu Vostinaru, Cluj-Napoca (RO); Ovidiu Ciprian Samoilă, Cluj-Napoca (RO); Elena Dinte, Cluj-Napoca (RO)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/399,388

(22) Filed: Apr. 30, 2019

(65) Prior Publication Data

US 2019/0254987 A1    Aug. 22, 2019

Related U.S. Application Data

(63) Continuation of application No. 15/502,415, filed as application No. PCT/US2015/044483 on Aug. 10, 2015, now Pat. No. 10,292,943.

(Continued)

(51) Int. Cl.
*A61K 31/047*      (2006.01)
*A61K 31/05*       (2006.01)
(Continued)

(52) U.S. Cl.
CPC .......... *A61K 31/047* (2013.01); *A61K 9/0048* (2013.01); *A61K 9/06* (2013.01);
(Continued)

(58) Field of Classification Search
None
See application file for complete search history.

(56) References Cited

U.S. PATENT DOCUMENTS

| 6,573,299 B1 | 6/2003 | Petrus ........................... 514/558 |
| 10,292,943 B2 * | 5/2019 | Sabliov ................ A61K 9/5169 |

(Continued)

FOREIGN PATENT DOCUMENTS

| CN | 103 845 278 A | 6/2014 |
| EP | 0386960 | 3/1990 |

(Continued)

OTHER PUBLICATIONS

Baghaei, B. et al., "Novel Thermosensitive Hydrogel Composites Based on Poly(D, I-lactide-co-glycolide) Nanoparticles Embedded in Poly(n-isopropyl acrylamide) With Sustained Drug-Release Behavior," Applied Polymer Science, vol. 131, No. 16, 40625 (2014).

(Continued)

*Primary Examiner* — Aradhana Sasan
(74) *Attorney, Agent, or Firm* — John H. Runnels

(57) ABSTRACT

Methods and compositions are disclosed for delivering lutein or other antioxidant to target tissues such as the eye, in bioactive form, while protecting the antioxidant from degradation. The antioxidant is encapsulated in nanoparticles comprising a protein such as zein or a polymer such as poly(lactic-co-glycolic acid) (PLGA). Preferably a surfactant is associated with the nanoparticles as well, further helping to protect the antioxidant. After the nanoparticles are administered to the target tissue, bioactive antioxidant is released to the tissue over time. Optionally, the nanoparticles (Continued)

are admixed with a thermosensitive, bioadhesive gel to promote slow release of antioxidant. The methods and compositions are useful for treating or preventing conditions such as age-related macular degeneration or cataracts.

18 Claims, 4 Drawing Sheets

Related U.S. Application Data

(60) Provisional application No. 62/172,455, filed on Jun. 8, 2015, provisional application No. 62/035,683, filed on Aug. 11, 2014.

(51) Int. Cl.
| | | |
|---|---|---|
| *A61K 9/00* | (2006.01) | |
| *A61K 9/06* | (2006.01) | |
| *A61K 47/34* | (2017.01) | |
| *A61K 9/51* | (2006.01) | |
| *A61K 47/10* | (2017.01) | |
| *A61K 47/24* | (2006.01) | |
| *A61P 27/12* | (2006.01) | |
| *A61K 9/19* | (2006.01) | |

(52) U.S. Cl.
CPC .......... *A61K 9/5146* (2013.01); *A61K 9/5153* (2013.01); *A61K 9/5169* (2013.01); *A61K 9/5192* (2013.01); *A61K 31/05* (2013.01); *A61K 47/10* (2013.01); *A61K 47/24* (2013.01); *A61K 47/34* (2013.01); *A61P 27/12* (2018.01); *A61K 9/0051* (2013.01); *A61K 9/19* (2013.01)

(56) References Cited

U.S. PATENT DOCUMENTS

| | | | |
|---|---|---|---|
| 2003/0050283 A1 | 3/2003 | Richter | 514/685 |
| 2004/0009212 A1 | 1/2004 | Tsai | 424/449 |
| 2010/0112073 A1 | 5/2010 | Sabliov et al. | 424/493 |
| 2012/0231072 A1 | 9/2012 | Kang-Mieler et al. | 424/451 |

FOREIGN PATENT DOCUMENTS

| | | |
|---|---|---|
| EP | 1534202 | 3/2009 |
| EP | 2594140 | 5/2013 |
| WO | WO 02/45683 | 6/2002 |
| WO | WO 2007/046083 | 4/2007 |
| WO | WO 2012/028733 | 3/2012 |
| WO | WO 2012/116282 | 8/2012 |

OTHER PUBLICATIONS

Elzoghby, A. et al., "Protein-Based Nanocarriers as Promising Drug and Gene Delivery Systems," Journal of Controlled Release, vol. 161, pp. 38-49 (2012).

Hao, J. et al., "Fabrication of a Composite System Combining Solid Lipid Nanoparticles and Thermosensitive Hydrogel for Challenging Ophthalmic Drug Delivery," Colloids and Surfaces β: Biointerfaces, vol. 114, pp. 111-120 (2014).

Hu, D. et al., "Preparation, Characterization, and In Vitro Release Investigation of Lutein/Zein Nanoparticles via Solution Enhanced Dispersion by Supercritical Fluids," Journal of Food Engineering, vol. 109, pp. 545-552 (2012).

Kamil, A. et al., "Bioavailability and Biodistribution of Nanodelivered Lutein," Food Chemistry, vol. 192, pp. 915-923 (2016).

Lim, A. et al., "Stability and Loss Kinetics of Lutein and β-Carotene Encapsulated in Freeze-Dried Emulsions with Layered Interface and Trehalose as Glass Former," Food Research International, vol. 62, pp. 403-409 (2014).

Sunkireddy, et al., "Natural Antioxidant Biomolecules Promises Future Nanomedicine Based Therapy for Cataract," Colloids and Surfaces B: Biointerfaces, vol. 112, pp. 554-562 (2013).

Lou, J. et al., "Optimization and Evaluation of a Thermoresponsive Ophthalmic In Situ Gel Containing Curcumin-Loaded Albumin Nanoparticles," International Journal of Nanomedicine, vol. 9, pp. 2517-2525 (2014).

Mitri, K. et al., "Lutein Nanocrystals as Antioxidant Formulation for Oral and Dermal Delivery," International Journal of Pharmaceutics, vol. 420, pp. 141-146 (2011).

Mitri, K. et al., "Lipid Nanocarriers for Dermal Delivery of Lutein: Preparation, Characterization, Stability and Performance," International Journal of Pharmaceutics, vol. 414, pp. 267-275 (2011).

Tan, C. et al., "Liposomes as Vehicles for Lutein: Preparation, Stability, Liposomal Membrane Dynamics, and Structure," Journal of Agricultural and Food Chemistry, vol. 61, pp. 8175-8184 (2013).

R. Bone et al., "Distribution of macular pigment components, zeaxanthin and lutein, in human retina," *Methods in Enzymology*, vol. 213, pp. 360-366 (1992).

L. Ma et al., "Effects of lutein and zeaxanthin on aspects of eye health," *J. Sci. Food. Agric.*, vol. 90, pp. 2-12 (2009).

J. Stringham et al., "The influence of dietary lutein and zeaxanthin on visual performance," *Journal of Food Science*, vol. 75, pp. R24-R29 (2010).

R. van der Veen et al., "Macular pigment optical density relates to foveal thickness," *European Journal of Ophthalmology*, vol. 19, pp. 836-841 (2009).

\* cited by examiner

DELIVERY OF BIOACTIVE, NANOENCAPSULATED ANTIOXIDANTS

This is a continuation of application Ser. No. 15/502,415, 35 U.S.C. § 371(c) date Feb. 7, 2017, now allowed with the issue fee paid; which is the United States national stage of international application PCT/US2015/044483, international filing date Aug. 10, 2015; which claimed the benefit under 35 U.S.C. § 119(e) of the filing dates both of U.S. provisional application 62/035,683, filed Aug. 11, 2014, and of U.S. provisional application 62/172,455, filed Jun. 8, 2015.

This invention was made with Government support under contract number 2010-05269 awarded by the National Institute of Food and Agriculture, United States Department of Agriculture. The United States Government has certain rights in the invention.

TECHNICAL FIELD

This invention pertains to methods and compositions to enhance the delivery of bioactive lutein or other antioxidants to tissues, and methods to make compositions that are useful for the enhanced delivery of bioactive lutein or other antioxidants to tissues, particularly to the eye and components of the eye such as the cornea and the retina.

BACKGROUND ART

Lutein

Lutein is a plant pigment, a xanthophyll, a dihydroxy carotenoid. The IUPAC name for lutein is β,ε-carotene-3,3'-diol; and its structure is:

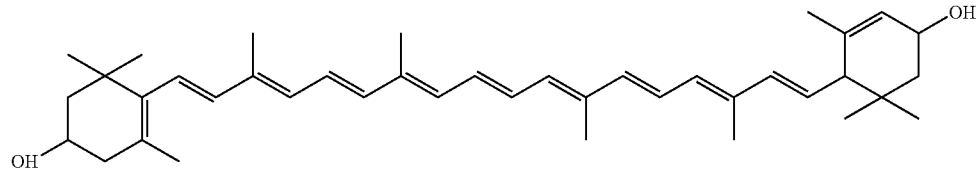 [SMILES: CC1=CC(O)CC(C)(C)C1/C=C/C(C)=C/C=C/C(C)=C/C=C/C=C(C)/C=C/C=C(C)/C=C/C1=C(C)CC(O)CC1(C)C]

Because humans are not capable of synthesizing carotenoids in vivo, the lutein in human tissues is normally of dietary origin. Lutein is found, for example, in green plants (e.g., alfalfa, wheat grass, barley grass, kale, spinach, broccoli, green beans, green peas, lima beans, cabbage, collards, mustard greens, and turnip greens), certain flowers (e.g., marigold flower petals), certain yellow fruits and vegetables (e.g., carrots, peaches, mango, papaya, squash, and oranges), egg yolks, chicken skin, and chicken fat. In maize for example, lutein is found primarily in the horny endosperm. Marigold flower petals (*Tagetes erecta*) are also an excellent source of lutein, albeit more expensive than lutein derived from maize.

Lutein has a sequence of ten conjugated carbon-carbon double bonds. The conjugated structure allows lutein to function as a primary antioxidant in a biological system by scavenging radicals such as peroxyl radicals, but the extensive conjugation also makes lutein susceptible to degradation by light, oxygen, and heat. The susceptibility to degradation makes it challenging to deliver lutein to tissues where needed.

The hydroxyl groups make lutein more polar than its unmodified β-carotene analog. Lutein is soluble in both nonpolar and polar solvents. See Table 1.

TABLE 1

Lutein: Physical Properties and Solubility in Various Solvents

A. Physical Properties of Lutein

| | |
|---|---|
| Molecular formula | $C_{40}H_{56}O_2$ |
| Molecular weight | 568.85 |
| Melting point | 183-190° C. |
| Appearance | Yellow prisms with metallic luster |
| Stability | Unstable to light and oxygen; Stable if stored at −20° C. under a nitrogen atmosphere |
| Solubility in water | Insoluble |

B. Solubility of Lutein in Organic Solvents

| Solvent | Solubility (mg/L) |
|---|---|
| Acetone | 800 |
| Acetonitrile | 100 |
| Benzene | 600 |
| Chloroform | 6000 |
| Cyclohexane | 50 |
| Cyclohexanone | 4000 |
| Dimethyl formamide | 1000 |
| Ethyl alcohol | 300 |
| Ethyl acetate | 800 |
| Ethyl ether | 2000 |
| Hexane | 20 |
| 2-Propanol | 400 |
| Methyl alcohol | 200 |
| Methyl tert butyl ether | 2000 |

TABLE 1-continued

Lutein: Physical Properties and Solubility in Various Solvents

| | |
|---|---|
| Tetrahydrofuran | 8000 |
| Toluene | 500 |

Adapted from J. I. X. Antony et al., "Lutein," The World of Food Ingredients, April/May, pp. 64-67 (2001)

The Role of Lutein in Health and Disease

Lutein decreases the risk of certain diseases and reduces the symptoms of certain diseases, particularly eye diseases such as Age-Related Macular Degeneration (AMD), and angiogenic-related diseases such as breast cancer and colon cancer. AMD is a degenerative condition of the region of the retina that is responsible for central vision. AMD is the most common cause of irreversible vision loss among older people. The carotenoids in the eye are concentrated in the inner retinal layer of the macula. Evidence from human studies suggest that dietary intake of carotenoids can lead to their accumulation in the retina, and is believed to provide protection against retinal degeneration. However, lutein is water-insoluble, making it difficult to effectively deliver bioactive lutein to target tissues, such as the retina, in a bioactive form without degradation. There is an unfilled need for methods and compositions to effectively deliver bioactive lutein or other antioxidants to target tissues, such as the retina, in a living organism in a bioactive form without degradation. To the inventors' knowledge, there have been no prior reports of any composition that is adapted for topical administration to the eye to deliver lutein to the interior of the eye, including the retina.

Lutein protects retinal pigment epithelial cells (RPE) from photo-oxidative damage through its ability to absorb short wavelength blue light, especially around 445 nm. Lutein can also modulate inflammation, and can help at least partially break the vicious cycle between oxidative stress and inflammatory response in RPEs. Furthermore, because lutein can quench singlet oxygen, lutein can help inhibit conditions resulting from oxidative stress, such as cardiovascular disease, stroke, lung cancer, breast cancer, and colon cancer. Lutein has a low water solubility, poor in vivo absorption, and low bioavailability. There is an unfilled need for improved delivery systems to take advantage of lutein's potential as an antioxidant, and to improve its physico-chemical stability during processing and storage.

Mitri, K.; Shegokar, R.; Gohla, S.; Anselmi, C.; Muller, R. H., Lipid nanocarriers for dermal delivery of lutein: preparation, characterization, stability and performance. *International journal of pharmaceutics* 2011, 414 (1-2), 267-75 discloses the use of lipid nanocarriers for dermal delivery of lutein, for example for use as a dermal anti-oxidant, anti-stress agent, or blue light filter. The lipid nanocarriers tested included solid lipid nanoparticles, nanostructured lipid carriers, and a nanoemulsion. Permeation studies with fresh pig ear skin showed that no or very little lutein permeated, leading to an inference that the active lutein remained in the skin but was not systemically absorbed.

Tan, C.; Xia, S.; Xue, J.; Xie, J.; Feng, B.; Zhang, X., Liposomes as vehicles for lutein: preparation, stability, liposomal membrane dynamics, and structure. *Journal of agricultural and food chemistry* 2013, 61 (34), 8175-8184 reports observations on the effect of lutein on liposome membrane stability, for potential uses of nano-encapsulated lutein in nutraceuticals and functional foods.

Mitri, K.; Shegokar, R.; Gohla, S.; Anselmi, C.; Muller, R. H., Lutein nanocrystals as antioxidant formulation for oral and dermal delivery. *International journal of pharmaceutics* 2011, 420 (1), 141-6 discloses the use of high pressure homogenization to prepare lutein nanosuspensions. The lutein nanosuspension was converted into pellets and filled into gelatin capsules for use as a nutraceutical. A lyophilized suspension was incorporated into creams or gels. When tested on pig ear skin as a model for potential dermal use, the lutein did not permeate through the skin.

Hu, D.; Lin, C.; Liu, L.; Li, S.; Zhao, Y, Preparation, characterization, and in vitro release investigation of lutein/zein nanoparticles via solution enhanced dispersion by supercritical fluids. *Journal of Food Engineering* 2012, 109 (3), 545-552 describes the use of supercritical fluids to enhance solution dispersion in the production of lutein/zein nanoparticles.

Elzoghby, A. O.; Samy, W. M.; Elgindy, N. A., Protein-based nanocarriers as promising drug and gene delivery systems. *Journal of Controlled Release* 2012, 161 (1), 38-49 provides a review of the use of protein-based nanocarriers as potential candidates for drug and gene delivery.

Lim, A. S. L.; Griffin, C.; Roos, Y. H., Stability and loss kinetics of lutein and β-carotene encapsulated in freeze-dried emulsions with layered interface and trehalose as glass former. *Food Research International* 2014, 62 (0), 403-409 discloses the formation of dehydrated emulsions of carotenoids such as β-carotene and lutein, for potential use in infant formulas, nutritional supplements, and medical foods. Layer-by-layer systems were found to retain the carotenoids better than single-layer emulsions, although the layer-by-layer systems also increased isomerization.

Kamil, A.; Smith, D. E.; Blumberg, J. B.; Astete, C.; Sabliov, C.; Chen, C.-Y. O., Bioavailability and biodistribution of nanodelivered lutein. *Food Chemistry* 2016, 192, 915-923 (available online 23 Jul. 2015) discloses the synthesis of poly(lactic-co-glycolic acid) nanoparticles containing lutein, and the plasma pharmacokinetics and deposition of lutein in selected tissues that followed administration of the nanoparticles by gastric gavage in a slurry that also contained olive oil, flour, and water.

Zein is a naturally-occurring protein that has been used in synthesizing nanodelivery systems. Zein is "generally recognized as safe" (GRAS) for human consumption by the United States Food and Drug Administration (FDA). Because zein is hydrophobic, it can be used as a carrier for the entrapment, controlled release, and stabilization of fat-soluble compounds. Zein nanoparticles have been synthesized with entrapped drugs, antimicrobial agents, and bioactive compounds such as 5-fluorouracil, thymol, curcumin, essential oils, and lutein.

There remains an unfilled need for improved compositions and methods for delivering bioactive lutein or other antioxidants to tissues where needed, such as the eye, while protecting the lutein or other antioxidant from degradation before it is delivered to such tissues.

DISCLOSURE OF INVENTION

We have discovered a novel method for topically delivering lutein or other antioxidants to target tissues such as the eye (including delivery of lutein to the retina) in bioactive form, while protecting the lutein or other antioxidant from degradation. The lutein or other antioxidant is encapsulated in nanoparticles comprising a protein such as zein or a synthetic polymer such as poly(lactic-co-glycolic acid) (PLGA). Preferably a surfactant is associated with the nanoparticles as well, further helping to protect the lutein or other antioxidant. After the nanoparticles are administered to the target tissue, bioactive lutein or other antioxidant is released to the tissue over time. Preferably the nanoparticles are admixed with a thermosensitive, bioadhesive gel to promote slow release of lutein or other antioxidant.

In one set of experiments we examined the ability of zein-based nanoparticles to protect lutein from oxidation and to control the release of lutein, both in the absence and in the presence of surfactant. Our hypothesis was that electrostatic affinity between the zein nanoparticles and surfactant molecules produces a more sustained release of lutein, and improves the chemical stability of the entrapped bioactive lutein. Lutein-loaded zein nanoparticles were synthesized using a liquid-liquid dispersion process, either with or without surfactant. A combination of phospholipid soybean lecithin and the tri-block copolymer Pluronic F127 was used as surfactant. Other surfactants could also be used, for example Tween™ 80 and other surfactants in the Tween™ family. "Conventional" emulsions containing lutein were prepared as controls. Dynamic light scattering (DLS) and transmission electron microscopy (TEM) were used to characterize particle physical stability. Lutein release and lutein degradation from nanoparticles suspended in PBS were measured both in the absence and presence of surfactant. Thermal- and photo-oxidation of lutein were also measured as indicators of chemical stability. Nanoparticles measured 156.1±18 nm without, and 216.5±29 nm with surfactant. Surfactant improved the polydispersity index, decreased the zeta potential, and improved entrapment efficiency. A two-phase release profile was observed: an initial burst release over 24 hours, which was smaller in the presence of surfactants; followed by a gradual zero-order release profile for systems both with and without surfactant. Lutein degradation followed second-order kinetics, with no significant differences between nanoparticles suspended in PBS and emulsified controls. Incorporating lutein into nanoparticles improved the stability of lutein against both thermal and UV stress, especially in the presence of surfactant. These data showed that the zein-based nanoparticles, especially with surfactant added, can efficiently entrap the hydrophobic lutein, while retaining lutein's bioactivity and protecting lutein against degradation, allowing for its slow release under physiological conditions.

In one embodiment, polymeric (PLGA) nanoparticles were used to deliver bioactive lutein to the eye. Bioactive lutein administered to the eye can be beneficial for such uses as inhibiting cataracts or macular degeneration. Preliminary results from a rat model were encouraging. Our preliminary results showed that the polymeric nanoparticles successfully delivered lutein to the eye, and provided therapeutic benefit.

MODES FOR CARRYING OUT THE INVENTION

Figure 1:
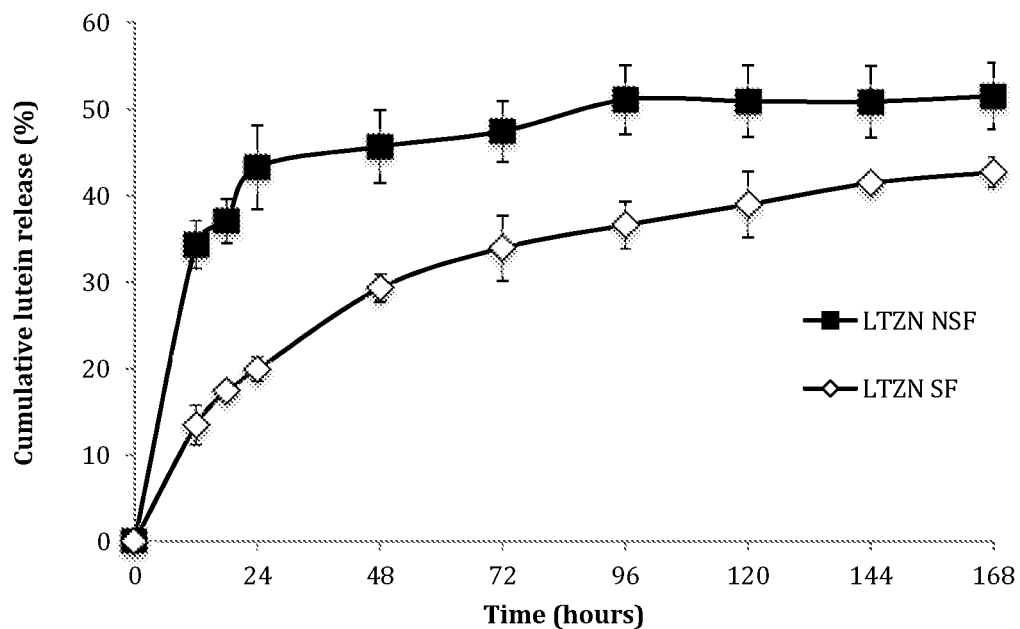
FIG. 1 depicts release kinetics of lutein from zein nanoparticles, with and without surfactant, in PBS solution (pH 7.4) at 37° C., 100 rpm for 7 days.

Zein-Entrapped Lutein Nanoparticles.

Little has previously been reported concerning the stability of lutein entrapped in zein nanoparticles under various processing and storage conditions, nor concerning the effect of surfactants on the release and stability of the lutein. We have studied lutein's thermal stability, its photo-stability, and its release from zein nanoparticles, both in the presence and absence of surfactant (lecithin and Pluronic F127 co-surfactants). Our hypotheses were that lutein entrapped in zein nanoparticles was more stable under various storage conditions, and that the electrostatic affinity between the zein nanoparticles and surfactant resulted in a more sustained release of lutein and improved the stability of the entrapped bioactive lutein.

Materials

Example 1

Zein, Pluronic F127, chloroform, ethanol, pepsin and pancreatin were purchased from Sigma-Aldrich (Sigma Chemical Co. Ltd., St. Louis, Mo.). Soybean lecithin, hydrochloric acid, and sodium hydroxide were purchased from Fisher Chemical (Fisher Scientific International, Fairlawn, N.J.). Lutein was provided by Kemin Foods, L. C. (Iowa, USA). Nanopure water was obtained using Nanopure Diamond 100 kDa Cellulose Ester Biotech membrane tubing (Barnstead international, IA, USA), and closures were purchased from Spectrum Laboratories Inc. (CA, USA). All other reagents and components used were analytical grade.

Methods

Example 2: Synthesis of Zein Nanoparticles with Entrapped Lutein

Nanoparticles were synthesized by liquid-liquid dispersion. 10 mg zein was dissolved in 1 ml ethanol-aqueous solution (70:30, v/v). A 0.75 mg/ml lutein solution was prepared in 100% ethanol, which was added dropwise to the zein solution at a 1:1 ratio (v/v) under mild stirring conditions. The mixture was then injected into 7.5 ml of an aqueous phase containing a combination of lecithin and Pluronic F127 0.045%:0.09% (w/v) as surfactants. The sample was then processed in a microfluidizer at 30,000 PSI for 3 cycles (M-110P, Microfluidics, MA, USA). Subsequently, ethanol was evaporated under partial vacuum (at approximately 500-600 mmHg) and nitrogen injection (80 mm Hg) in a rotovapor (Buchi R-124, Buchi Analytical Inc., DE, USA). The lutein-loaded zein nanoparticles remaining after the complete evaporation of ethanol were washed by dialysis using a 100 kDa Spectra/POR CE membrane (Spectrum Rancho, Calif., USA). The nanoparticle suspension was placed in the membrane and suspended in 1.5 L nanopure water for 24 hours total time; the dialysis medium (water) was changed every 4-6 hours to remove free surfactant. The suspension was collected and kept at room temperature for further analysis. Zein nanoparticles without surfactant were prepared in parallel following otherwise identical procedures. Finally, a lutein emulsion made with surfactant only (no zein nanoparticles) served as a control.

Characterization of Zein Nanoparticles

Example 3: Particle Size, Polydispersity Index (PDI), and Zeta Potential

Freshly-prepared nanoparticle samples were characterized by measuring average particle size, PDI, and zeta potential by dynamic light scattering (DLS), using a Malvern Zetasizer Nano ZS (Malvern Instruments Ltd., Worcestershire, U.K.). Before the measurements were made, samples were diluted to a final concentration range of 0.2-0.32 mg/ml. Citrate buffer at pH 7.4 (0.1 M) was added to stabilize the samples and to inhibit particle aggregation. All measurements were performed in triplicate.

Example 4: Morphology

Morphology of freshly-made zein nanoparticles was observed by transmission electron microscopy (TEM). One droplet of the sample was placed on a copper grid of 400 mesh with a carbon film, and excess sample was absorbed with filter paper. Uranyl acetate was used as a negative stain to improve the contrast of the sample.

Example 5: Entrapment Efficiency (EE)

A 1.0 mL sample of freshly-made, lutein-loaded zein nanoparticles was centrifuged at 30,000 rpm for 75 min. The supernatant and the nanoparticle-containing pellet were collected. Both samples were broken by ethanol, and lutein was then extracted with chloroform (1:1 ratio). The solubility of lutein in chloroform (6000 mg/L) is 20 times higher than its solubility in ethanol (300 mg/L). The concentration of lutein was measured with a UV/Vis spectrophotometer in a glass cell, 1 cm path length, absorption measured at 445 nm. The absorbance value was converted to lutein concentration based on a standard curve for lutein in 1:1 ethanol and chloroform. Encapsulation efficiency (%) was estimated as the ratio of the amount of lutein in the pellet to the theoretical amount of lutein available for entrapment. All measurements were performed in triplicate.

Example 6: Lutein Release from Zein Nanoparticles in Phosphate-Buffered Saline (PBS)

We studied the release of entrapped lutein from zein nanoparticles in phosphate-buffered saline (PBS) solution (pH 7.4 at 37° C.); 0.5% Tween 20 was added to the PBS to improve the solubility of the released lutein. Briefly, 10 ml of freshly-prepared nanoparticles were added to 20 ml of Tween 20-enhanced PBS, and mixed thoroughly. The mixture was divided and placed into 1 ml centrifuge tubes, which in turn were placed in a shaking incubator (C25KC incubator shaker, New Brunswick Scientific, NJ, USA) at 37° C., 100 rpm. At predetermined times, a centrifuge tube was sampled and centrifuged at 30,000 rpm for 75 min. The supernatant was removed and extracted with ethanol and chloroform (2 ml:2 ml), and then vortexed for 10 minutes. The extracted lutein was determined in the supernatant by measuring absorbance at 445 nm using a UV/Ms spectrophotometer as otherwise described under entrapment efficiency section. All measurements were performed in triplicate.

Example 7: Lutein Degradation from Zein Nanoparticles Suspended in PBS

The degradation of lutein entrapped in zein nanoparticles (with and without surfactant), and of lutein in the surfactant-stabilized emulsion was determined by measuring the amount of lutein detected in the pellet and the amount of lutein in the supernatant under the same conditions.

Example 8: Physical Stability of Zein Nanoparticles with Entrapped Lutein

Freshly-made samples were stored in the dark at three different temperatures: 4° C. in a refrigerator, 25° C. room temperature, and 40° C. in an incubator over one month. Samples were monitored for changes in average particle size, surface characteristics, and fraction entrapped after 7, 15, and 30 days of storage. All experiments were performed in triplicate.

Example 9: Photo-Chemical Stability of Lutein Entrapped in Zein Nanoparticles

Nanoparticle and emulsion samples were stored in transparent glass vials in a lightproof cabinet, where they were exposed to 365 nm UV lamps (100 W: Blak-Ray model B 100AP) for up to 10 hours. After intervals of 0.5, 1, 2, 3, 5, 7, and 10 hours, 1 ml was withdrawn from each sample and then extracted and analyzed for lutein concentration using UV-Vis spectrophotometer at 445 nm. The experiments were performed in triplicate.

Example 10: Degradation Reaction Kinetics

A general description of the reaction rate for lutein degradation and release can be given as $$\frac{d[C]}{dt} = -k[C]^n;$$

where C is the lutein concentration, k is the reaction rate constant, and n is the order of the reaction. The correlation coefficient ($R^2$) was used to determine the best fit of the kinetic models. The degradation of lutein by UV exposure followed first-order kinetics:

$$\ln\left(\frac{[C]}{[C_0]}\right) = -kt.$$

When stored in PBS, lutein degradation followed second-order kinetics:

$$\frac{1}{[C]} = \frac{1}{[C_0]} + kt,$$

where C was the concentration of lutein at time t, $C_0$ was the initial concentration of lutein, t was the time, and k was the reaction rate as derived from the slope of linear regression analysis.

Example 11: Statistical Analysis of Data

All experiments were performed in triplicate, and results were reported as mean±standard error. Statistical analyses were performed with SAS software (version 9.4, SAS Institute Inc., NC, USA). Analysis of variance (ANOVA) was used to determine significant differences between systems. The significance level (p) was set at 0.05.

Results and Discussions

Example 12: Physicochemical Characterization

Liquid-liquid dispersion was successfully used to synthesize lutein-loaded zein nanoparticles, both with and without surfactant. The surfactant used to stabilize the nanoparticles in these prototype experiments was a combination of lecithin and Pluronic™ F127. Lecithin, a natural food emulsifier or stabilizer, has a hydrophilic head, phosphatidylcholine (PC); and two hydrophobic tails, phosphatidylethanolamine (PE) and phosphotidylinositol (PI). Pluronic™ F127 is a hydrophilic, non-ionic surfactant copolymer with a hydrophobic block of polypropylene between two hydrophilic blocks of polyethylene glycol. We hypothesize that one or more layers of lecithin cover the surface of the hydrophobic zein nanoparticles, with lutein entrapped inside. The hydrophilic head of the lecithin associates with the hydrophilic polyethylene glycol moieties of Pluronic™ F127; and the hydrophobic polypropylene moiety possibly associates with the zein matrix. The result is a hydrophilic zein nanoparticle loaded with hydrophobic lutein, which may be used to disperse the bioactive lutein in an aqueous environment, while protecting it from degradation.

Lutein-loaded zein nanoparticles, and otherwise similar nanoparticles without lutein, in both cases either with or without surfactant, were characterized immediately after purification. See Table 2. Average particle size, PDI, and zeta potential of freshly-made samples were measured after 24 hours dialysis in citrate buffer (pH 7.4). The average particle size of lutein loaded in zein nanoparticles, with or without surfactant, was 217±29 nm or 156±18 nm, respectively. Zein nanoparticles with surfactant had a relatively small polydispersity (less than 0.3). Without surfactant, a higher PDI range of 0.33-0.48 was observed.

TABLE 2

Characteristics of unloaded and lutein (LT)-loaded zein (ZN) nanoparticles, with surfactant (SF) or without surfactant (NSF).

| Sample[a] | Size (nm) | PDI (a.u.) | Zeta Potential (mV) | EE (%) |
|---|---|---|---|---|
| ZN SF | 208.8 ± 8.0 | 0.19 ± 0.04 | −47.6 ± 1.6 | — |
| LTZN SF | 216.5 ± 29 | 0.26 ± 0.09 | −30.9 ± 3.3 | 83.0 ± 5.8 |
| ZN NSF | 149.2 ± 5.5 | 0.48 ± 0.07 | −31.9 ± 4.3 | — |
| LTZN NSF | 156.1 ± 18 | 0.33 ± 0.06 | −21.0 ± 8.6 | 69.1 ± 11.4 |

Note:
Values are expressed as mean ± standard error (n = 3).
[a]Mass ratio of zein to lutein was 1:0.075 (w/w), and mass ratio of lecithin to Pluronic F127 was 1:2 (w/v).

The results were confirmed by transmission electron microscopy (TEM) (data not shown). Particles with surfactant had a spherical shape with a rough surface, and some particles were connected to one another by a surfactant "mesh." Nanoparticles without surfactant were smaller in size, with a more spherical morphology, but were less uniform in size and more likely to agglomerate, resulting in higher PDI values as measured by dynamic light scattering.

Zeta potential is a measure of nanoparticle stability. A high degree of stability is expected at zeta potentials above about +30 mV, or below about −30 mV. Particles with surfactant were found to be more negatively charged (−47.6±1.6 mV) than particles without surfactant (−31.9±4.3 mV), indicating a good stability for the surfactant-stabilized particles. Entrapped lutein reduced the magnitude of the zeta potential to −30.9±3.3 mV with surfactant or −21.0±8.6 mV without surfactant. The hydrophobic interaction between lutein and zein presumably rearranged the zein structure, resulting in the observed zeta potential change.

Without surfactant, entrapment efficiency was 69.1±11.4%. With surfactant, entrapment efficiency increased to 83±5.8%.

Example 13: Release and Release Mechanism. Lutein Release from Zein Nanoparticles in PBS Phosphate buffered saline (PBS) is commonly used for testing drug release. FIG. 1 depicts release kinetics of lutein from zein nanoparticles, with and without surfactant, in PBS solution (pH 7.4) at 37° C., 100 rpm for 7 days. The release profile followed a two-phase pattern, with an initial-burst release over 24 hours, followed by zero-order release after 24 hours. See Table 3. For particles without surfactant (LTZN NSF), 43% of the lutein was released in the initial-burst phase. For particles with surfactant (LTZN SF), only 20% of the lutein was released in the initial-burst phase. The surfactant retarded lutein release. Release of lutein after 24 hours followed zero-order kinetics. See Table 4 below. For particles without surfactant, 52% lutein was released after 168 hours, versus only 43% for particles with surfactant. Hydrophobic interactions promoted by the surfactant inhibited the hydrolytic degradation of zein, and slowed the release of lutein. In the absence of surfactant, rapid protein swelling resulted in a faster release of the entrapped bioactive by diffusion through aqueous channels forming in the hydrated, swollen zein matrix. Surfactant resulted in a more sustained release of lutein.

Example 14: Lutein Degradation in PBS

Figure 2:
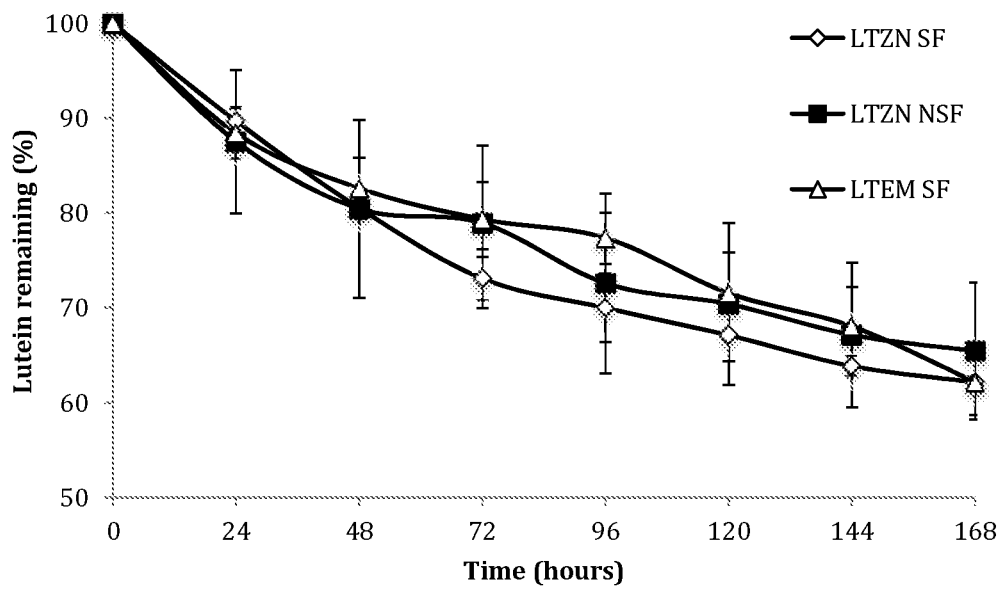
FIG. 2 depicts lutein retention in zein nanoparticles both with (LTZN SF) and without surfactants (LTZN NSF), and comparable observations for lutein emulsified with surfactant (LTEM SF). All measurements were carried out in PBS solution (pH 7.4) at 37° C., 100 rpm for 7 days.

Lutein tends to be more susceptible to degradation from heat and other causes than are many other carotenes, due to its conjugated double bonds and its two hydroxyl groups. We assessed the degradation of lutein entrapped in zein nanoparticles both with (LTZN SF) and without surfactants (LTZN NSF); those observations were compared to comparable observations for lutein emulsified with the same surfactants (LTEM SF). All measurements were carried out in PBS solution (pH 7.4) at 37° C., 100 rpm for 7 days. See FIG. 2. Lutein degradation profiles followed second-order kinetics, with no significant differences in the degradation rate constant (k) among the systems studied. See also Table 4 below.

Examples 15 and 16: Nanoparticle Chemical and Physical Stability, as a Function of Time and as a Function of Temperature We observed the physical stability of zein nanoparticles at 4° C., 25° C., and 40° C. over 30 days by measuring size, PDI, and zeta potential. Chemical stability of entrapped lutein was assessed in parallel, by measuring the absorbance at 445 nm. See Table 3. Zein nanoparticles, both with and without surfactant, were stable at low temperature, measuring between 156.1±18 and 216.5±29 nm when stored at 4° C. for 30 days. The nanoparticles tended to increase in size over time when stored at higher temperatures, especially without surfactant. For example, the size of nanoparticles with surfactant increased to 380.5±51 nm following 30 days of storage at 25° C. By contrast, the size of particles without surfactant increased much more, to 3103±332 nm following 30 days of storage at 25° C. At 40° C., particles larger than 1 μm could be detected after only 7 days of storage without surfactant. The PDI generally increased with temperature and storage time (from 0.27 to 0.80). Zeta potential ranged from −18 mV to −25 mV for nanoparticles without surfactant, and from −15 mV to −38 mV for particles with surfactant.

TABLE 3

Characteristics of lutein-loaded zein nanoparticles at different temperatures after storage for 30 days.

| Sample | Temperature | Time | Size (nm) | PDI (a.u) | Zeta Potential (mV) |
|---|---|---|---|---|---|
| LTZN SF | 4° C. | 0 d | 216.5 ± 50 | 0.27 ± 0.05 | −30.9 ± 3.3 |
| | | 7 d | 195.7 ± 19 | 0.29 ± 0.05 | −31.1 ± 10.8 |
| | | 15 d | 183.0 ± 26 | 0.27 ± 0.06 | −32.2 ± 10.7 |
| | | 30 d | 168.6 ± 2 | 0.27 ± 0.04 | −33.0 ± 10.8 |
| | 25° C. | 0 d | 216.5 ± 50 | 0.27 ± 0.05 | −30.9 ± 3.3 |
| | | 7 d | 170.8 ± 65 | 0.38 ± 0.05 | −23.3 ± 2.4 |
| | | 15 d | 221.0 ± 74 | 0.35 ± 0.06 | −21.8 ± 9.5 |
| | | 30 d | 380.8 ± 51 | 0.36 ± 0.07 | −15.2 ± 0.3 |
| | 40° C. | 0 d | 216.5 ± 50 | 0.27 ± 0.05 | −30.9 ± 3.3 |
| | | 7 d | 134.5 ± 40 | 0.54 ± 0.07 | −38.0 ± 1.9 |
| | | 15 d | 203.1 ± 49 | 0.24 ± 0.06 | −31.8 ± 7.4 |
| | | 30 d | 229.5 ± 27 | 0.29 ± 0.03 | −29.5 ± 2.9 |
| LTZN NSF | 4° C. | 0 d | 156.1 ± 18 | 0.26 ± 0.06 | −21.0 ± 8.6 |
| | | 7 d | 142.4 ± 32 | 0.32 ± 0.11 | −23.8 ± 1.0 |
| | | 15 d | 189.2 ± 55 | 0.26 ± 0.07 | −24.6 ± 1.7 |
| | | 30 d | 198.9 ± 47 | 0.39 ± 0.13 | −25.0 ± 2.6 |
| | 25° C. | 0 d | 156.1 ± 18 | 0.26 ± 0.06 | −21.0 ± 8.6 |
| | | 7 d | 567.7 ± 203 | 0.56 ± 0.07 | −24.6 ± 1.7 |
| | | 15 d | 1406.1 ± 79 | 0.47 ± 0.13 | −23.7 ± 1.5 |
| | | 30 d | 3103 ± 332 | 0.58 ± 0.15 | −23.6 ± 1.4 |

TABLE 3-continued

Characteristics of lutein-loaded zein nanoparticles at different temperatures after storage for 30 days.

| Sample | Temperature | Time | Size (nm) | PDI (a.u) | Zeta Potential (mV) |
|---|---|---|---|---|---|
| | 40° C. | 0 d | 156.1 ± 18 | 0.26 ± 0.06 | −21.0 ± 8.6 |
| | | 7 d | 1096.1 ± 53 | 0.58 ± 0.05 | −18.0 ± 2.7 |
| | | 15 d | 2434.5 ± 35 | 0.73 ± 0.19 | −21.0 ± 0.6 |
| | | 30 d | 3599.5 ± 94 | 0.80 ± 0.10 | −22.7 ± 4.2 |

Note:
Values are expressed as mean ± standard error (n = 3).

Figure 3A:
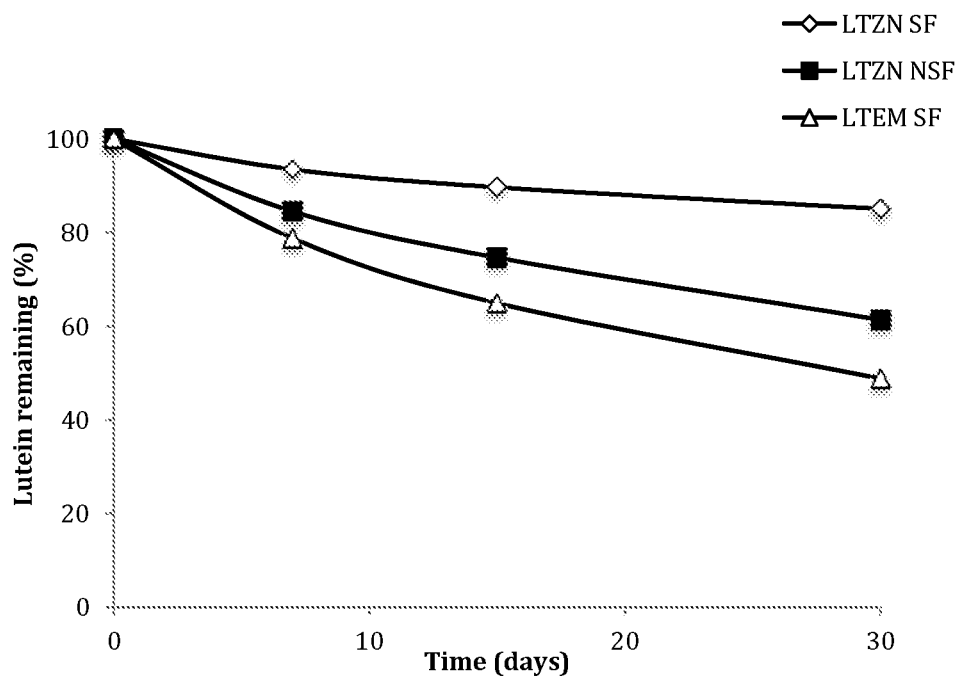
FIGS. 3A through 3C depict lutein retention in zein nanoparticles as a function of time at different temperatures.
Figure 3B:
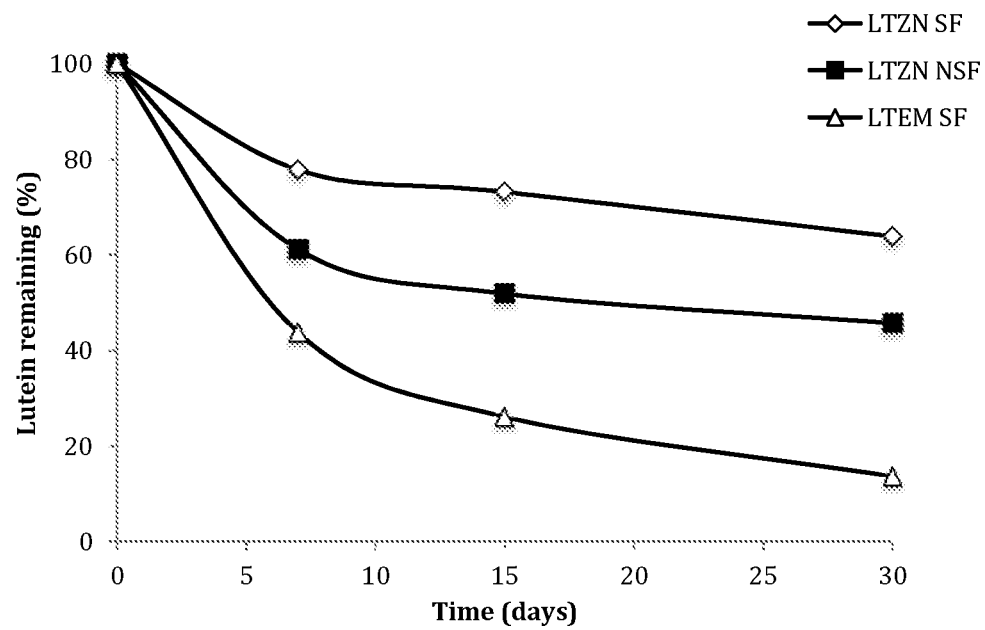
Figure 3C:
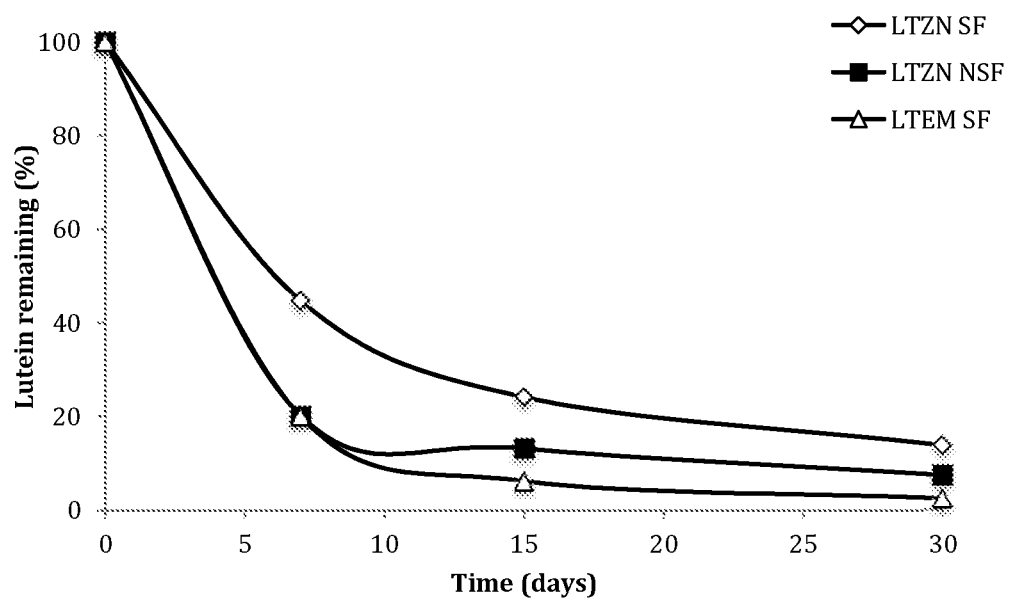

The surfactants not only provided long-term storage stability for at least 30 days, but they also delayed the degradation of lutein. See FIGS. 3A through 3C. Only 26% of entrapped lutein LTZN SF had degraded after 30 days at 25° C., compared to 54% for LTZN NSF. Similar trends were seen at 40° C. for both types of particles; 13.8% and 7.5% of lutein remained in the nanoparticles with and without surfactant, respectively. At all temperatures, emulsified lutein degraded faster than lutein entrapped in zein nanoparticles. Lutein degradation at all temperatures followed second-order kinetics. See Table 4. At each storage temperature, the lowest degradation rate was seen for lutein-loaded zein nanoparticles with surfactant. Degradation rates increased at higher temperatures for all systems.

Example 17: Photo-Chemical Stability Against UV Exposure

Figure 4:
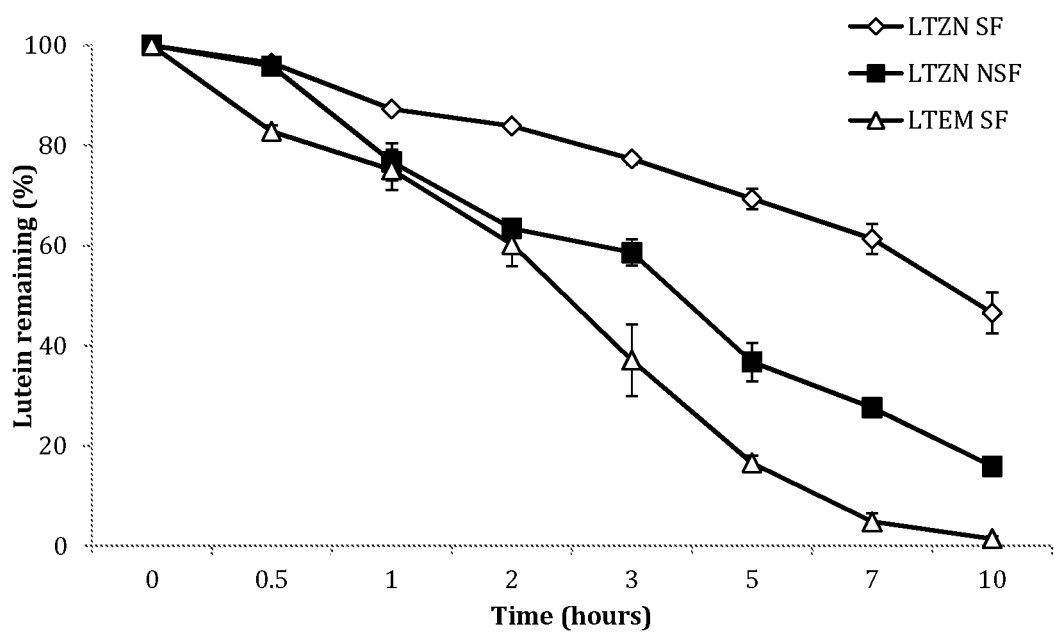
FIG. 4 depicts retention of lutein as a function of time for different compositions in response to UV-induced degradation.

The zein nanoparticles enhanced the photochemical stability of lutein against UV-induced degradation; and the addition of surfactant to the nanoparticles enhanced stability further. Emulsified lutein underwent rapid photochemical degradation. See FIG. 4. After 10 h, only 1.4% entrapped lutein remained in the lutein emulsion, compared to 15.9% for lutein in zein nanoparticles without surfactant, and 46.6% for lutein in zein nanoparticles with surfactant. See also Table 4. Photochemical degradation followed first-order decay in all cases.

Without wishing to be bound by this hypothesis, we believe that competitive absorption of UV photons by zein was responsible for the enhanced photochemical stability observed for lutein entrapped in zein nanoparticles. Zein absorbs UV, especially its aromatic amino acids such as phenylalanine. Surfactants such as lecithin associated with zein nanoparticles also improved lutein stability against UV. Without wishing to be bound by this hypothesis, we believe that rapid energy transfer from the excited lutein species to lecithin promotes stability against UV. Overall, the entrapped lutein was significantly more resistant to UV degradation in zein nanoparticles with combined lecithin and Pluronic F127 surfactants.

TABLE 4

A best-fit model for release and degradation of lutein loaded in zein nanoparticles.

| Experiment | Sample | | Time | Kinetic model | K | $R^2$ |
|---|---|---|---|---|---|---|
| Release | LTZN SF | | 0-24 h | Zero-order | 0.90930 | 0.95203 |
| | LTZN NSF | | | (Initial burst) | 2.02800 | 0.88626 |
| | LTZN SF | | 24-168 h | Zero-order | 0.00120 | 0.83448 |
| | LTZN NSF | | | | 0.01270 | 0.92693 |
| Degradation | LTZN SF | | 168 h | $2^{nd}$ order | 0.00004 | 0.96389 |
| | LTZN NSF | | | | 0.00003 | 0.91575 |
| | LTEM SF | | | | 0.00003 | 0.97666 |
| Physical stability | LTZN SF | 4° C. | 30 d | $2^{nd}$ order | 0.00006 | 0.92430 |
| | | 25° C. | | | 0.00020 | 0.84325 |
| | | 40° C. | | | 0.00210 | 0.99788 |
| | LTZN NSF | 4° C. | 30 d | $2^{nd}$ order | 0.00020 | 0.99243 |
| | | 25° C. | | | 0.00050 | 0.75685 |
| | | 40° C. | | | 0.00420 | 0.98458 |
| | LTEM SF | 4° C. | 30 d | $2^{nd}$ order | 0.00040 | 0.99878 |
| | | 25° C. | | | 0.00210 | 0.99502 |
| | | 40° C. | | | 0.01210 | 0.96126 |
| Photochemical stability | LTZN SF | | 10 h | $1^{st}$ order | 0.07530 | 0.98454 |
| | LTZN NSF | | | | 0.18690 | 0.99256 |
| | LTEM SF | | | | 0.40930 | 0.98301 |

"LTEM SF" denotes the formulation of emulsified lutein-zein nanoparticles made with surfactants.

Discussion.

We synthesized zein nanoparticles loaded with 7.5% lutein stabilized with a combined lecithin/Pluronic F127 surfactant, using a solvent-free, liquid-liquid dispersion method. Adding the surfactants increased particle size slightly, and improved the polydispersity index. The zeta potential changed slightly, and the entrapment efficiency increased significantly with the surfactants. An initial rapid release of lutein decreased in samples with surfactant as compared to samples without surfactant; a decrease in early, "burst" release is beneficial for sustained release. Zein nanoparticles protected lutein from degradation under various storage conditions, as compared to lutein that was simply emulsified. Lutein-loaded zein nanoparticles with surfactants could be stored at 4° C. for at least 30 days, with little loss of activity. The nanoparticle/surfactant formulation protected lutein against degradation by UV light for at least 10 hours.

Polymeric (PLGA) Nanoparticles Containing Lutein to Inhibit Cataracts

In one embodiment, polymeric nanoparticles in accordance with the invention are used to deliver lutein to the eye. Lutein administered to the eye can be beneficial for such uses as inhibiting cataracts or inhibiting macular degeneration. Our preliminary results from a rat model are encouraging. Our preliminary results showed that the polymeric nanoparticles could successfully deliver lutein to the eye and deliver therapeutic benefit.

Selenite-induced cataract in the rat is a rapid and convenient model for nuclear cataracts. Administering selenite to suckling rat pups induces cataracts. Several biochemical mechanisms are believed to be involved, including loss of calcium homeostasis, calpain-induced proteolysis, crystallin precipitation, and cytoskeletal loss. Lutein's antioxidant properties could help to inhibit at least some of these pathways. The novel topical formulation of lutein, entrapped in polymeric nanoparticles, especially when complemented by a bioadhesive formulation, enhanced the ocular bioavailability of lutein and increased its therapeutic efficacy.

Future experiments in animal models of macular degeneration will confirm the efficacy of the novel formulation of lutein for inhibiting the progress of macular degeneration. Models of age related macular degeneration (AMD) have been developed, for example, in mice, rats, rabbits, pigs, and non-human primates. See for example Penessi M E, Neuringer M, Courtney R J. Animal models of age-related macular degeneration. Mol Aspects Med. 2012, 33(4): 487-509. There are at least four rodent models of macular degeneration. One model relies on an inactivated SOD1 gene (SOD1−/− mice). See Imamura Y, Noda S, Hashizume K, Shinoda K, Yamaguchi M, Uchiyama S, Shimizu T, Mizushima Y, Shirasawa T, Tsubota K. Drusen, choroidal neovascularization, and retinal pigment epithelium dysfunction in SOD1-deficient mice: a model of age-related macular degeneration. Proc. Nat. Acad. Sci. USA. 2006; 103(30): 11282-11287. Another model relies on an inactivated ApoE gene (ApoE −/− mice). See Dithmar S, Sharara N A, Curcio C A, Le N A, Zhang Y, Brown S, Grossniklaus H E. Murine high-fat diet and laser photochemical model of basal deposits in Bruch membrane. Arch. Ophthalmol. 2001; 119(11): 1643-1649. A different type of model relies on aging mice (16 months) fed a high-fat diet. See Cousins S W, Espinosa-Heidmann D G, Alexandridou A, Sall J, Dubovy S, Csaky K. The role of aging, high fat diet and blue light exposure in an experimental mouse model for basal laminar deposit formation. Exp. Eye Res. 2002; 75(5):543-553. Still another model relies on ultraviolet induction of macular degeneration. See Pavelic S C et al. UV-induced retinal proteome changes in the rat model of age-related macular degeneration. Biochimica et Biophysica Acta-Molecular Basis of Disease. 2015, 1852 (9):1833-1845. The first two models may be better suited for testing the effect of the lutein-loaded nanoparticles on potential disease remission. The last two models may be better suited for testing effect of the lutein-loaded nanoparticles in protecting against the development of AMD. In each case, lutein would be administered as lutein-loaded polymeric nanoparticles in bioadhesive hydrogel, topically applied to the cornea.

Methods

Example 18

In one embodiment, lutein-containing poly(lactic-co-glycolic) acid (PLGA) nanoparticles were synthesized by a modified emulsion/evaporation method. Briefly, 100 mg PLGA was dissolved in 10 ml of ethyl acetate, and 10 mg lutein was added under mild stirring. The mixture was then added dropwise at room temperature to 80 ml of an aqueous solution of Tween™ 80 (4 mg/ml) saturated with ethyl acetate. After 5 minutes of stirring, the sample was processed with a microfluidizer at 30,000 psi (~200 MPa) for 3 cycles (M-110P, Microfluidics, MA, USA). Subsequently, the solvent was evaporated under vacuum and nitrogen injection in a rotovapor (Buchi R-124, Buchi Inc., DE, USA). The lutein-loaded PLGA nanoparticles were dialyzed with a 100 kDa Spectra/POR CE membrane (Spectrum Rancho, Calif., USA) against water for 24 hours, with three water changes to remove free surfactant. Finally, trehalose (3:1 w/w) was added to the PLGA nanoparticle suspension, and the sample was lyophilized with a freeze dryer (Labconco, Kansas City, Mo.) for 48 hours at −80° C. The nanoparticle powder was stored at −20° C. until used.

Example 19

In another embodiment, lutein-containing poly(lactic-co-glycolic) acid (PLGA) nanoparticles were synthesized by a slightly different emulsion/evaporation method. These nanoparticles were used in our first set of animal studies (Examples 25-38). Briefly, 400 mg PLGA 50:50 copolymer with a molecular weight of 30-60 kDa (Sigma-Aldrich, St. Louis, Mo.) was dissolved in 8 mL of ethyl acetate; and 40 mg lutein was added after the polymer had dissolved, to produce the organic phase. The organic phase was mixed with 60 mL of 2% polyvinyl alcohol (PVA) in water (aqueous phase), and then microfluidized (Microfluidics Inc., Westwood, Mass.) at 25,000 psi (~170 MPa) four times in an ice bath. The solvent was evaporated with a Rotovapor Buchi R-124 (Buchi Labortechnik AG, Switzerland) under $N_2$ gas. Next the nanoparticle suspension was dialyzed for 48 hours (with water replaced every 8 hours) using a Spectra/Por CE cellulose ester membrane with a 100 kDa molecular weight cut off (Spectrum Rancho, Dominguez, Calif.). Finally, trehalose (Sigma-Aldrich, St. Louis, Mo.) was added (1:1 w/w theoretical ratio) before freezing the suspension. The sample was freeze-dried for 40 h using a Freezone 2.5 Plus freeze-drier (Labconco, Kansas City, Mo.).

Example 20

In yet another embodiment, lutein-containing poly(lactic-co-glycolic) acid (PLGA) nanoparticles were synthesized by a slightly different emulsion/evaporation method. These nanoparticles were used in our second set of animal studies (Examples 39-53). Briefly, 100 mg PLGA was dissolved in 10 ml ethyl acetate, and 10 mg lutein was then added under mild stirring. The mixture was then added dropwise to 80 ml of an aqueous solution of Tween™ 80 (4 mg/ml) saturated with ethyl acetate at room temperature. After 5 minutes of stirring, the sample was processed with a microfluidizer at 30,000 PSI (~200 MPa) for 3 cycles (M-110P, Microfluidics, MA, USA). Subsequently, the solvent was evaporated under vacuum and nitrogen injection in a rotovapor (Buchi R-124, Buchi Inc., DE, USA). The lutein-loaded PLGA nanoparticles were dialyzed with a 100 kDa Spectra/POR CE membrane (Spectrum Rancho, Calif., USA) against water for 24 hours with three water changes to remove free surfactant. Finally, trehalose (3:1 w/w) was added to the PLGA nanoparticle suspension, and the sample was lyophilized with a freeze dryer (Labconco, Kansas City, Mo.) for 48 hours at −80° C. The nanoparticle powder was stored at −20° C. until used.

Example 21

In another embodiment, zein-lutein nanoparticles were synthesized by liquid-liquid dispersion. Briefly, 500 mg zein was dissolved in 15 ml of an acetone-water solution (70:30, v/v). Next, lutein was added to the acetone-water solution under mild stirring conditions, to 3 mg/ml final concentration. The mixture was then injected into 110 ml of an aqueous solution of Tween™ 80 (3 mg/ml). The sample was then processed in a microfluidizer at 30,000 PSI (~200 MPa) for 3 cycles (M-110P, Microfluidics, MA, USA). Subsequently, the solvent was evaporated under partial vacuum (at approximately 500-600 mmHg) and nitrogen injection (80 mm Hg) in a rotovapor (Buchi R-124, Buchi Analytical Inc., DE, USA). Finally, trehalose was added to the lutein-loaded zein nanoparticle suspension at a mass ratio 1:3, and the samples were freeze-dried for 2 days at −80° C. The resulting powder was stored at −20° C. until used.

Example 22

We examined the morphology of the lutein-containing poly(lactic-co-glycolic) acid (PLGA) nanoparticles from Examples 19 and 20 by transmission electron microscopy (TEM) using a JEOL 100-CX system (JEOL USA Inc., Peabody, Mass.). Briefly, samples were prepared as follows: 500 μL of nanoparticle suspension was mixed with a contrast agent (negative staining, one droplet of 2% uranyl acetate solution). One droplet of the mixture was placed on a carbon-coated copper grid, 400 mesh. Excess of the sample was removed with filter paper, and the liquid film on the grid was dried at room temperature for 15 min before placing the grid in the microscope. The PLGA nanoparticles were observed to be generally spherical and to be uniformly distributed, without significant agglomeration.

Example 23

We examined particle size, polydispersity index (PI), and zeta potential of the lutein-containing poly(lactic-co-glycolic) acid (PLGA) nanoparticles from Example 19 by dynamic light scattering (DLS) using a Malvern Zetasizer Nano ZS (Malvern Instruments Inc., Southborough, Mass.). Resuspended PLGA-lutein nanoparticle samples were diluted to 0.5 mg/ml. Nanoparticle mean size was measured as 124±4 nm. PI was measured as 0.11±0.09. Zeta potential was measured as −5.3±1.9 mV at pH 6.5. All samples were measured in triplicate.

Example 24

We measured lutein entrapment efficiency of the nanoparticles from Example 19 by UV-Vis spectrophotometry. Briefly, 6 mg PLGA-lutein nanoparticle powder was resuspended in 600 μL of water by sonication, followed by addition of 5.4 mL of acetonitrile. The mixture was vortexed for 4 hours and centrifuged at 30,000×g for 15 minutes at 4° C. to obtain a white pellet. The supernatant was collected, and absorbance was measured at 450 nm with a UV-vis spectrophotometer (Genesys 6, ThermoFisher Scientific, Waltham, Mass.) to obtain lutein concentration. The samples and standard curve were measured in triplicate. The measured lutein entrapment efficiency was 52±3%.

Example 25

Preparation of the in situ bioadhesive gel formulations containing suspended lutein-containing PLGA nanoparticles:

The in situ bioadhesive gel used in these experiments as a vehicle for the lutein-entrapped nanoparticles comprised a mixture of 2.7% (w/w) bioadhesive polymer (polyethylene oxide, Polyox™ 1105, Dow Chemical, MW ~900,000), and 16.5% (w/w) Poloxamer P407 (a triblock copolymer comprising a central hydrophobic block of polypropylene glycol, flanked by two hydrophilic blocks of polyethylene glycol; the approximate lengths of the two PEG blocks was 101 repeat units, and the approximate length of the propylene glycol block was 56 repeat units). The polyethylene oxide— Poloxamer P407 mixture readily forms a thermoreversible gel. The Polyethylene oxide 1105 and the Poloxamer P407 were each separately dispersed in sterile water until used. The Polyethylene oxide/Poloxamer mixture was prepared by mixing the dispersions, and it the mixture was stored in a refrigerator (4° C.) until used. The lutein-containing nanoparticles were later added to the bioadhesive in situ gel forming matrix under continuous, gentle stirring.

The bioadhesive matrix may optionally comprise another polymer, copolymer, or mixture of polymers or copolymers with bioadhesive properties, including for example polyacrylic acid derivatives, cellulose derivatives, polycarbophil, other polyethylene oxides, hyaluronic acid derivatives, pectin, carrageenan, alginates, and the like. It is preferred that the matrix should be bioadhesive, it should be thermosensitive (to form a gel and release nanoparticles slowly at body temperature, or more specifically the temperature of the conjunctival sac), it should be well-tolerated by ocular mucosa, it should be compatible with the nanoparticles, it should facilitate controlled and reproducible release of the dispersed bioactive ingredient, and it should exhibit prolonged retention following topical administration.

The preferred bioadhesive matrix combination of poloxamer and polyethylene oxide provides several beneficial properties and features: Poloxamer is compatible with the ocular mucosa. The poloxamer is a thermoreversible polymer which, at higher concentrations and temperatures forms a stable, rigid gel that would, by itself, be difficult to apply topically. At lower temperatures, the polymer stays in aqueous solution—a liquid. As the temperature rises, the polymer forms a gel. Preferably the composition is a liquid at room temperature, but becomes a gel at body temperature (or more specifically, at the temperature of the conjunctival sac, which may be 2-3 degrees below body temperature), allowing for the slow release of the active ingredient once the composition forms a gel on the surface of the cornea. Polyethylene oxides have good adhesive qualities. Polyethylene oxide 1105 (with a small to medium molecular weight range) is a preferred compound due to its rheological characteristics. Polyethylene oxides are also compatible with ocular mucosa. A mixture of poloxamer and polyethylene oxide provides a product that is easily applied as a liquid to the cornea, into the conjunctival sac, and that forms a gel following contact with the conjunctiva at body temperature. The mixture has enhanced bioadhesive properties, for extended retention following topical administration, and thus improved bioavailability of lutein to the eye—including the interior of the eye and the retina. These nonionic polymers should not exhibit incompatibilities with the bioactive components.

Although it is preferred to administer the nanoparticles as drops that can form a thermoreversible gel as described above, other routes of administration may also be used. The polymeric components optionally may be omitted. Other pharmaceutical formulations otherwise known in the art may optionally be used—e.g., liquid eye preparations (eye drops, eye lotions, gel-forming solutions); semisolid eye preparations (ointments, gels); solid eye preparations (powders, ocular inserts); or aerosols (ophthalmic drugs mixed with a gas under pressure).

II preparations were aseptically manufactured in a laminar air flow hood, and were stored in previously sterilized containers. No preservatives were added to any of the preparations.

Through routine experimentation to test various proportions, the ratios and concentrations of the various components are being optimized to enhance residence time on and penetration into the cornea. Typical ranges that have been tested in embodiments to date have included polyethylene oxide 1105 in a range of 1.5-3.5% (w/w), and Poloxamer P407 in a range of 12-19% (w/w).

The bioadhesive matrix should produce a good dispersion of nanoparticles, it should have sufficient viscosity to maintain homogeneity during storage (physical stability), it should allow ready application on conjunctival mucosa, and it should be compatible with the substances used in the preparation of nanoparticles.

Depending on the concentration of the nanoparticles in the ophthalmic preparation, the bioadhesive/thermosensitive polymer's concentration can be adjusted to optimize viscosity and bioadhesive capacity. The needed w/v % of embodied lutein-containing nanoparticles depends on their load in lutein. To date we have tested lutein loadings in the bioadhesive gel primarily in the range 1-5% w/v %. Higher and lower concentrations can also be tested or used.

Other bioadhesive gel-forming matrices may be prepared by mixing suitable polymers in appropriate proportions. Examples of bioadhesive polymers include one or more of polyacrylic acid, polycarbophil, polyethylene oxides, cellulose derivatives, hyaluronic acid derivatives, pectin, carrageenan, alginates, and the like. The molecular weight may be chosen to optimize performance.

Examples 26-32: Animal Treatments

Four pregnant Wistar female albino rats were obtained from the Laboratory Animal Facility of the Iuliu Hatieganu University of Medicine and Pharmacy in Cluj-Napoca, Romania. Each female rat and its litter of pups were housed in plastic cages, on a 12 h lighting cycle, at constant temperature (22° C.) with free access to rat chow and tap water. At 12 days of age, the rat pups were randomized into seven groups as follows:

Group 1 (selenite group, positive control): no exposure to lutein

Group 2 (PLGA-NP-1) daily received orally, by gavage, 2.5 mg/kg PLGA-NP-lutein dispersed in a 0.5 mL emulsion of 30% olive oil+70% flour slurry, corresponding to a daily dose of 2.66 mg lutein/kg body mass. (The flour slurry, in turn, had been prepared by mixing 0.3 g flour in 1 ml water.)

Group 3 (PLGA-NP-2) daily received orally, by gavage, 5 mg/kg PLGA-NP-lutein dispersed in 0.5 mL emulsion of 30% olive oil+70% flour slurry, corresponding to a daily dose of 5.32 mg lutein/kg body mass. (Flour slurry: identical to that used for Group 2

Group 4 (lutein) daily received orally, by gavage, 0.00525 mg unmodified lutein dispersed in 0.5 mL emulsion of 30% olive oil+70% flour slurry, corresponding to a daily dose of 0.125 mg lutein/kg body mass. (Flour slurry: identical to that used for Group 2.)

Group 5 (HG-PLGA-NP-1) was treated locally, once a day, with corneal application (1 drop in each eye) of 1 wt % PLGA-NP-lutein in the bioadhesive hydrogel of Example 19. (30 mg of lyophilized lutein-loaded PLGA NPs were dissolved in 3 ml of bioadhesive hydrogel. The volume of one drop of hydrogel was approx. 0.012 mL, with a density of 0.9444 g/mL.)

Group 6 (HG-PLGA-NP-2) was treated locally, once a day, by corneal application (1 drop/in each eye) with 3% PLGA-NP-lutein in a bioadhesive hydrogel. (90 mg of lyophilized lutein-loaded PLGA NPs were dissolved in 3 ml of bioadhesive hydrogel. The volume of one drop of hydrogel was approx. 0.012 mL, with a density of 0.9444 g/mL.)

Group 7 (negative control)—no exposure to selenite, and no lutein treatment.

On day 13 post-partum, cataracts were induced in all animals in Groups 1-6 with a single, intraperitoneal injection of sodium selenite ($Na_2SeO_3$), 30 μmol/kg. Subsequently, the animals from groups 2-6 were treated daily, in accordance with the protocols described above. The lutein content of the PLGA-NPs (42.61 μg lutein/mg PLGA-NP) was assessed by UV-VIS spectrophotometry (450 nm) with an external standard calibration. On day 21 post-partum, cataract development was evaluated by slit-lamp examination. Eyes were scored into one of five stages: stage 0 (no cataract), stage 1 (slight nucleus opacity), stage 2 (mild nucleus opacity, a central while opacity occupying less than half the diameter of the nucleus), stage 3 (dense opacity, a central while opacity occupying more than half the diameter of the nucleus) and stage 4 (dense, white opacity over the whole nucleus). Statistics were performed in SPSS 14.0 for Windows and Excel. The variables were checked for normal distribution with the Shapiro-Wilk test. Groups were compared with the Wilcoxon test. Statistical significance was set at $p<0.05$.

All biological experiments were approved by the Ethics Commission of the Iuliu Hatieganu University of Medicine and Pharmacy Cluj-Napoca, and were conducted according to EC directive 86/609/EEC regulating the use of laboratory animals.

Results

Examples 33-39

Table 5 shows the observed distribution of cataract severity for the various Groups. All animals in the negative control group showed no symptoms of cataracts (stage 0). All animals in the selenite positive control group developed bilateral, stage 4 cataracts.

TABLE 5

Observed distribution of cataract severity for the various Groups of rat pups, day 21 postpartum

| Group | N | Stage 0 (no. animals) | Stage 1 (no. animals) | Stage 2 (no. animals) | Stage 3 (no. animals) | Stage 4 (no. animals) | Cataract stage Mean ± SD |
|---|---|---|---|---|---|---|---|
| 1: Selenite | 5 | 0 | 0 | 0 | 0 | 5 | 4.0 ± 0.0 |
| 2: PLGA-NP-1 | 5 | 0 | 1 | 1 | 0 | 3 | 3.0 ± 1.4 |
| 3: PLGA-NP-2 | 6 | 0 | 0 | 1 | 2 | 3 | 3.3 ± 0.8 |
| 4: Lutein | 5 | 0 | 0 | 1 | 2 | 2 | 3.2 ± 0.8 |
| 5: HG-PLGA-NP-1 | 5 | 0 | 0 | 4 | 1 | 0 | 2.2 ± 0.4* |
| 6: HG-PLGA-NP-2 | 5 | 0 | 2 | 1 | 1 | 1 | 2.2 ± 1.3* |
| 7: Control | 5 | 5 | 0 | 0 | 0 | 0 | 0.0 ± 0.0 |

*(statistically significant difference from Group 1, $p < 0.05$)

In group 2, treated orally with 62.5 mg/kg PLGA-NP-lutein (equivalent to a dose of 2.66 mg lutein/kg), three animals developed stage 4 cataracts, one developed stage 2 cataracts, and one developed stage 1 cataracts. In group 3, treated orally with 125 mg/kg PLGA-NP-lutein (equivalent to a dose of 5.32 mg lutein/kg), three animals developed stage 4 cataracts, two developed stage 3 cataracts, and one developed stage 2 cataracts. In group 4, treated orally with 0.125 mg/kg lutein, two animals developed stage 4 cataracts, two stage 3 cataracts and one stage 2 cataracts. In group 5, treated locally with 1% PLGA-NP-lutein in the bioadhesive hydrogel, one animal developed stage 3 cataracts, and the other four animals developed stage 2 cataracts. In group 6, treated locally with 3% PLGA-NP-lutein in the bioadhesive hydrogel, one animal developed stage 4 cataracts, one animal developed stage 3 cataracts, one animal developed stage 2 cataracts, and two animals developed only stage 1 cataracts.

Discussion

A single injection of selenite induced stage 4 nuclear cataracts in 100% of the positive control animals in group 1. None of the animals from negative control group 7 developed cataracts. Because the positive and negative controls both responded in the manner expected, we could exclude the possibility of complicating factors from environmental influences. Only a small (and statistically insignificant) reduction in cataract development was seen in animals treated orally with lutein alone, or treated orally with lutein entrapped in polymeric nanoparticles. However, a substantial and significant reduction in in cataract development was seen in animals treated locally with a corneal application of the novel topical bioadhesive formulation, with lutein entrapped in polymeric nanoparticles.

These results showed that the novel formulation is highly effective in delivering lutein to the eye in therapeutically effective concentrations. Lutein delivered by the novel formulation protected against selenite-induced cataract, likely by decreasing oxidative stress in all structural components of the eye. The topical bioadhesive formulation with lutein entrapped in polymeric nanoparticles increased the ocular bioavailability of lutein.

Examples 40-46: Further Animal Treatments

Nine pregnant Wistar female albino rats were obtained from the Laboratory Animal Facility of the Iuliu Hatieganu University of Medicine and Pharmacy in Cluj-Napoca, Romania. Each female rat and its litter of pups were housed in plastic cages, on a 12 h lighting cycle, at constant temperature (22° C.) with free access to rat chow and tap water. The pups of each female rat constituted one of the nine study groups as follows:

Group 1 (selenite group, positive control): no exposure to lutein

Group 2 (lutein—426) was treated locally, once a day, with a corneal application (1 drop in each eye) of unmodified lutein (426 µg lutein/ml) in the bioadhesive hydrogel. 3.21 mg finely ground pure lutein were dispersed by trituration into 7.53 ml of bioadhesive hydrogel. The volume of one drop of hydrogel was approx. 0.012 mL, with a density of 1.023 g/mL.) The final concentration of lutein (426 µg lutein/ml) was equivalent to 1 wt % lutein-loaded nanoparticles in the hydrogel. (The intention was that each of the animals in Groups 2, 4, and 7 would receive approximately the same concentration of lutein.)

Group 3 (lutein—2130) was treated locally, once a day, with corneal application (1 drop in each eye) of unmodified lutein (2130 µg lutein/ml) in the bioadhesive hydrogel. 11.99 mg finely ground pure lutein were dispersed by trituration into 5.63 ml of bioadhesive hydrogel. The volume of one drop of hydrogel was approx. 0.012 mL, with a density of 1.023 g/mL.) The concentration of lutein (2130 µg lutein/ml) was equivalent to 5 wt % lutein-loaded nanoparticles in the hydrogel.

Group 4 (PLGA-NP-lutein 426) was treated locally, once a day, by corneal application (1 drop in each eye) with 426 µg lutein/mL (from lutein-loaded PLGA nanoparticles, Example 20) in the bioadhesive hydrogel. 375.7 mg of lyophilized, lutein-loaded PLGA nanoparticles were dissolved in 15.25 ml of bioadhesive hydrogel. The volume of one drop of hydrogel was approx. 0.012 mL, with a density of 1.040 g/mL.

Group 5 (PLGA-NP-1278) was treated locally, once a day, by corneal application (1 drop in each eye) with 1278 µg lutein/mL (from lutein-loaded PLGA nanoparticles, Example 20) in the bioadhesive hydrogel. 379.9 mg of lyophilized, lutein-loaded PLGA nanoparticles were dissolved in 5.14 ml of bioadhesive hydrogel. The volume of one drop of hydrogel was approx. 0.012 mL, with a density of 1.040 g/mL.)

Group 6 (PLGA-NP-2130) was treated locally, once a day, by corneal application (1 drop in each eye) with 2130 µg lutein/mL (from lutein-loaded PLGA nanoparticles, Example 20) in the bioadhesive hydrogel. 376.7 mg of lyophilized, lutein-loaded PLGA nanoparticles were dissolved in 3.06 ml of bioadhesive hydrogel. The volume of one drop of hydrogel was approx. 0.012 mL, with a density of 1.040 g/mL.)

Group 7 (ZEIN-NP-426) was treated locally, once a day, by corneal application (1 drop in each eye) with 426 µg lutein/mL (from lutein-loaded zein nanoparticles, Example 21) in the bioadhesive hydrogel. 252.1 mg of lyophilized, lutein-loaded zein nanoparticles were dissolved in 8.81 ml of bioadhesive hydrogel. The volume of one drop of hydrogel was approx. 0.012 mL, with a density of 1.040 g/mL.

Group 8 (ZEIN-NP-1278) was treated locally, once a day, by corneal application (1 drop in each eye) with 1278 µg lutein/mL (from lutein-loaded zein nanoparticles, Example 21) in the bioadhesive hydrogel. 345.7 mg of lyophilized, lutein-loaded zein nanoparticles were dissolved in 4.03 ml of bioadhesive hydrogel. The volume of one drop of hydrogel was approx. 0.012 mL, with a density of 1.040 g/mL.

Group 9 (ZEIN-NP-2130) was treated locally, once a day, by corneal application (1 drop in each eye) with 2130 µg lutein/mL (from lutein-loaded zein nanoparticles, Example 21) in the bioadhesive hydrogel. 346.1 mg of lyophilized, lutein-loaded zein nanoparticles were dissolved in 2.42 ml of bioadhesive hydrogel. The volume of one drop of hydrogel was approx. 0.012 mL, with a density of 1.040 g/mL.

On day 13 post-partum, cataracts were induced in all animals in each of Groups 1-9 with a single, intraperitoneal injection of sodium selenite ($Na_2SeO_3$), 30 µmol/kg. Subsequently, the animals from groups 2-9 were treated daily, in accordance with the protocols described above. The lutein content of the PLGA-NPs (17.29 µg lutein/mg PLGA-NP) and ZEIN-NPs (14.89 µg lutein/mg ZEIN-NP) was assayed by UV-VIS spectrophotometry (445 nm) with an external standard calibration. On day 21 post-partum, cataract development was evaluated by slit-lamp examination. Eyes were scored into one of five stages: stage 0 (no cataract), stage 1 (slight nucleus opacity), stage 2 (mild nucleus opacity, a central while opacity occupying less than half the diameter of the nucleus), stage 3 (dense opacity, a central while opacity occupying more than half the diameter of the nucleus) and stage 4 (dense, white opacity over the whole nucleus). Statistics were performed in SPSS 14.0 for Windows and Excel. The variables were checked for normal distribution with the Shapiro-Wilk test. Groups were compared with the Wilcoxon test. Statistical significance was set at $p<0.05$.

All biological experiments were approved by the Ethics Commission of the Iuliu Hatieganu University of Medicine and Pharmacy Cluj-Napoca, and were conducted according to EC directive 86/609/EEC regulating the use of laboratory animals.

Results

Examples 48-54

Table 6 shows the observed distribution of cataract severity for the various Groups.

TABLE 6

Observed distribution of cataract severity for the various Groups of rat pups, day 21 postpartum

| Group | N | Stage 0 (no. examined eyes) | Stage 1 (no. examined eyes) | Stage 2 (no. examined eyes) | Stage 3 (no. examined eyes) | Stage 4 (no. examined eyes) | Cataract stage Mean ± SD |
|---|---|---|---|---|---|---|---|
| 1: Selenite | 18 | 3 | 2 | 1 | 8 | 4 | 2.44 ± 1.42 |
| 2: Lutein-426 | 14 | 2 | 4 | 3 | 5 | 0 | 1.79 ± 1.12 |
| 3: Lutein-2130 | 14 | 3 | 1 | 7 | 3 | 0 | 1.71 ± 1.07 |
| 4: PLGA-NP-426 | 18 | 6 | 3 | 4 | 3 | 2 | 1.56 ± 1.42 |
| 5: PLGA-NP-1278 | 20 | 15 | 3 | 0 | 1 | 1 | 0.50 ± 1.15* |
| 6: PLGA-NP-2130 | 10 | 4 | 2 | 0 | 3 | 1 | 1.50 ± 1.58 |
| 7: ZEIN-NP-426 | 20 | 6 | 7 | 4 | 1 | 2 | 1.30 ± 1.25 |
| 8: ZEIN-NP-1278 | 18 | 4 | 6 | 4 | 4 | 0 | 1.44 ± 1.10* |
| 9: ZEIN-NP-2130 | 14 | 4 | 5 | 3 | 2 | 0 | 1.21 ± 1.05* |

*(statistically significant difference from Group 1, p < 0.05)

According to the Saphiro Wilk test, none of the data sets were normally distributed. Therefore the Wilcoxon statistical test was applied. Due to the small number of pups in Group 6 (PLGA-NP-5), the data for Group 6 was not considered valid for further statistical evaluation. Groups 5 (PLGA-NP-1278), 8 (Zein-NP-1278) and 9 (Zein-NP-2130) showed statistical significant differences ($p<0.05$) from the controls. (Group 1).

Discussion

Comparing the lutein-treated groups (Groups 2-9) with the positive control group (Group 1), only groups 5, 8 and 9 (Group 5, p=0.001, Group 8, p=0.05; and Group 9, p=0.05) showed a statistically significant reduction in cataract development. By contrast, only a small and statistically insignificant reduction in cataract development was seen in the eyes of rat pups treated with unmodified lutein in the bioadhesive hydrogel, regardless of concentration (426 µg lutein/ml or 2130 µg lutein/ml). By contrast, lutein loaded into polymeric nanoparticles, and incorporated into a hydrogel successfully delivered lutein to the eye in therapeutically effective amounts (Groups 5, 8 and 9). Although Group 5 (PLGA-NP-1278) seemed to deliver the more favorable outcome, it was not statistically different (p=0.112) from Group 8 (ZEIN-NP-1278) having the same load of lutein in zein rather than PLGA nanoparticles.

Our results at this point show a clear beneficial effect for delivering lutein to the eye with a nanostructured polymeric vehicle incorporated into a bioadhesive hydrogel. However, it is premature to rank the two polymers used (zein and PLGA). Lutein delivered by the novel formulations successfully inhibited the effect of selenite-induced cataract, most likely by decreasing oxidative stress in the cornea. To the inventors' knowledge, this is the first report of the successful delivery of lutein to the eye in therapeutically effective concentrations by a topical formulation.

Example 55—Other Antioxidants

The prototype embodiments of this invention have employed lutein for delivery to the eye. The invention may also be used to deliver other antioxidants, such as beta-carotene, lycopene, retinol, and other carotenoids. The invention may be used to deliver antioxidants to other tissues where needed, for example to the skin.

MISCELLANEOUS

As used in the specification and claims, a "therapeutically effective amount" of a composition refers to a quantity of the composition sufficient to be therapeutically effective to prevent, inhibit, slow the progression, or treat the symptoms of a disease of the eye such as cataracts, dry macular degeneration or wet macular degeneration (age-related macular degeneration), Stargardt disease, or retinitis pigmentosa. Where appropriate in context, a "therapeutically effective amount" of a composition can also refer to a quantity of the composition that, when administered topically to a tissue, is sufficient to deliver a concentration of an antioxidant to the tissue to have a clinically meaningful effect on the tissue or neighboring tissues.

The complete disclosures of all references cited in this application are hereby incorporated by reference. Also, incorporated by reference are the complete disclosures of the two priority applications, U.S. provisional application 62/035,683, filed 11 Aug. 2014, and U.S. provisional application 62/172,455, filed 8 Jun. 2015. In the event of an otherwise irreconcilable conflict, however, the present specification shall control.

What is claimed:

1. A method for delivering lutein to the eye of a mammal, wherein the mammal has macular degeneration; said method comprising topically administering to the mammal's eye a composition that comprises a mixture of nanoparticles and a hydrogel:
   (a) wherein the nanoparticles comprise: (i) a synthetic polymer or a protein, (ii) lutein, and (iii) a surfactant; wherein the polymer or protein entraps the lutein; wherein the surfactant associates with the polymer or protein; wherein the nanoparticles have a diameter between 50 nm and 250 nm; wherein the nanoparticles are more hydrophilic than is native lutein; wherein the lutein in the nanoparticles has greater resistance to degradation by oxygen, to degradation by ultraviolet light, or both than does free lutein;
   (b) wherein the hydrogel comprises a mixture of water, a thermoreversible gel-forming polymer, and a bioadhesive polymer; wherein the composition is liquid at 25° C., wherein the thermoreversible gel-forming polymer causes the composition to become a gel at the temperature of the conjunctival sac or of the surface of the cornea of the mammal; and wherein the bioadhesive polymer causes the gel to adhere to the conjunctival mucosa and cornea more strongly than the gel would adhere without the bioadhesive polymer;
   (c) wherein the composition is applied as a liquid to the surface of the cornea or into the conjunctival sac; wherein the temperature of the conjunctival sac or of the surface of the cornea causes the composition to form a gel; wherein the gel adheres to the conjunctival mucosa, to the surface of the cornea, or both; and wherein the adhering gel releases lutein to the eye over a period of time; and
   (d) wherein the mammal has macular degeneration, and said method alleviates the symptoms of macular degeneration.

2. The method of claim 1, wherein the polymer or a protein comprises zein.

3. The method of claim 1, wherein the polymer or protein comprises poly(lactic-co-glycolic acid).

4. The method of claim 1, wherein the thermoreversible gel-forming polymer comprises a poloxamer.

5. The method of claim 1, wherein the bioadhesive polymer comprises a polyethylene oxide.

6. The method of claim 1, wherein said method results in the delivery of lutein to the retina.

7. A method for delivering lutein to the eye of a mammal, wherein the mammal is at risk for developing macular degeneration; said method comprising topically administering to the mammal's eye a composition that comprises a mixture of nanoparticles and a hydrogel:
   (a) wherein the nanoparticles comprise: (i) a synthetic polymer or a protein, (ii) lutein, and (iii) a surfactant; wherein the polymer or protein entraps the lutein; wherein the surfactant associates with the polymer or protein; wherein the nanoparticles have a diameter between 50 nm and 250 nm; wherein the nanoparticles are more hydrophilic than is native lutein; wherein the lutein in the nanoparticles has greater resistance to degradation by oxygen, to degradation by ultraviolet light, or both than does free lutein;
   (b) wherein the hydrogel comprises a mixture of water, a thermoreversible gel-forming polymer, and a bioadhesive polymer; wherein the composition is liquid at 25° C., wherein the thermoreversible gel-forming polymer causes the composition to become a gel at the temperature of the conjunctival sac or of the surface of the cornea of the mammal; and wherein the bioadhesive polymer causes the gel to adhere to the conjunctival mucosa and cornea more strongly than the gel would adhere without the bioadhesive polymer;
   (c) wherein the composition is applied as a liquid to the surface of the cornea or into the conjunctival sac; wherein the temperature of the conjunctival sac or of the surface of the cornea causes the composition to form a gel;
   wherein the gel adheres to the conjunctival mucosa, to the surface of the cornea, or both; and wherein the adhering gel releases lutein to the eye over a period of time; and
   (d) wherein the mammal is at risk for developing macular degeneration.

8. The method of claim 7, wherein the polymer or a protein comprises zein.

9. The method of claim 7, wherein the polymer or protein comprises poly(lactic-co-glycolic acid).

10. The method of claim 7, wherein the thermoreversible gel-forming polymer comprises a poloxamer.

11. The method of claim 7, wherein the bioadhesive polymer comprises a polyethylene oxide.

12. The method of claim 7, wherein said method results in the delivery of lutein to the retina.

13. A method for delivering lutein to the eye of a mammal, wherein the mammal is at risk for developing photo-oxidative damage to the mammal's retinal pigment epithelial cells; said method comprising topically administering to the mammal's eye a composition that comprises a mixture of nanoparticles and a hydrogel:
   (a) wherein the nanoparticles comprise: (i) a synthetic polymer or a protein, (ii) lutein, and (iii) a surfactant; wherein the polymer or protein entraps the lutein; wherein the surfactant associates with the polymer or protein; wherein the nanoparticles have a diameter between 50 nm and 250 nm; wherein the nanoparticles are more hydrophilic than is native lutein; wherein the lutein in the nanoparticles has greater resistance to degradation by oxygen, to degradation by ultraviolet light, or both than does free lutein;

(b) wherein the hydrogel comprises a mixture of water, a thermoreversible gel-forming polymer, and a bioadhesive polymer; wherein the composition is liquid at 25° C., wherein the thermoreversible gel-forming polymer causes the composition to become a gel at the temperature of the conjunctival sac or of the surface of the cornea of the mammal; and wherein the bioadhesive polymer causes the gel to adhere to the conjunctival mucosa and cornea more strongly than the gel would adhere without the bioadhesive polymer;

(c) wherein the composition is applied as a liquid to the surface of the cornea or into the conjunctival sac; wherein the temperature of the conjunctival sac or of the surface of the cornea causes the composition to form a gel; wherein the gel adheres to the conjunctival mucosa, to the surface of the cornea, or both; and wherein the adhering gel releases lutein to the eye over a period of time; and (d) wherein the mammal is at risk for developing for developing photo-oxidative damage to the mammal's retinal pigment epithelial cells; and wherein the lutein protects the retinal pigment epithelial cells by absorbing short wavelength blue light, including blue light of wavelength 445 nm.

14. The method of claim 13, wherein the polymer or a protein comprises zein.

15. The method of claim 13, wherein the polymer or protein comprises poly(lactic-co-glycolic acid).

16. The method of claim 13, wherein the thermoreversible gel-forming polymer comprises a poloxamer.

17. The method of claim 13, wherein the bioadhesive polymer comprises a polyethylene oxide.

18. The method of claim 13, wherein said method results in the delivery of lutein to the retina.

* * * * *